United States Patent
Ukil et al.

(10) Patent No.: US 11,531,830 B2
(45) Date of Patent: Dec. 20, 2022

(54) SYNTHETIC RARE CLASS GENERATION BY PRESERVING MORPHOLOGICAL IDENTITY

(71) Applicant: Tata Consultancy Services Limited, Mumbai (IN)

(72) Inventors: Arijit Ukil, Kolkata (IN); Soma Bandyopadhyay, Kolkata (IN); Chetanya Puri, Kolkata (IN); Rituraj Singh, Kolkata (IN); Arpan Pal, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1165 days.

(21) Appl. No.: 16/102,069

(22) Filed: Aug. 13, 2018

(65) Prior Publication Data
US 2019/0050673 A1    Feb. 14, 2019

(30) Foreign Application Priority Data
Aug. 14, 2017 (IN) .............................. 201721028875

(51) Int. Cl.
*G06K 9/62* (2022.01)
*A61B 5/1455* (2006.01)
*A61B 5/0205* (2006.01)
*G06N 7/08* (2006.01)
*G06N 20/00* (2019.01)
*G16H 50/70* (2018.01)
*G16C 20/70* (2019.01)

(52) U.S. Cl.
CPC ............ *G06K 9/623* (2013.01); *A61B 5/0205* (2013.01); *A61B 5/1455* (2013.01); *G06K 9/6257* (2013.01); *G06N 7/08* (2013.01); *G06N 20/00* (2019.01); *G16H 50/70* (2018.01); *G16C 20/70* (2019.02)

(58) Field of Classification Search
CPC ...... G06K 9/623; G06K 9/6257; G16H 50/70; G06N 20/00; G06N 7/08; A61B 5/0205; A61B 5/1455
USPC ......................................................... 706/12
See application file for complete search history.

(56) References Cited

PUBLICATIONS

Cao, H. et al. (2013). "Integrated Oversampling for Imbalanced Time Series Classification," *IEEE Transactions on Knowledge and Data Engineering*, vol. 25, issue 12; 14 pages.

(Continued)

*Primary Examiner* — Sath V Perungavoor
*Assistant Examiner* — Kristin Dobbs
(74) *Attorney, Agent, or Firm* — Finnegan, Henderson, Farabow, Garrett & Dunner LLP

(57) ABSTRACT

In many real-life applications, ample amount of examples from one class are present while examples from other classes are rare for training and learning purposes leading to class imbalance problem and misclassification. Methods and systems of the present disclosure facilitate generation of an extended synthetic rare class super dataset that is further pruned to obtain a synthetic rare class dataset by maximizing similarity and diversity in the synthetic rare class dataset while preserving morphological identity with labeled rare class training dataset. Oversampling methods used in the art result in cloning of datasets and do not provide the needed diversity. The methods of the present disclosure can be applied to classification of noisy phonocardiogram (PCG) signals among other applications.

8 Claims, 5 Drawing Sheets

```
analyzing a labeled abundant training dataset and labeled rare    202
                class training dataset
                            ↓
generating an extended rare class dataset based on the analysis   204
            using an extended oversampling method
                            ↓
extracting a subset of the extended rare class dataset to obtain
  a synthetic rare class dataset by maximizing similarity and
       diversity in the synthetic rare class dataset, wherein
      maximizing similarity ensures maximizing mutual            206
   information and maximizing diversity ensures minimum
    redundancy in the synthetic rare class dataset such that
 morphological identity of the synthetic rare class dataset is
    maintained with respect to the labeled rare class training
              dataset while maintaining diversity
```

(56) References Cited

PUBLICATIONS

Cao, H. et al. (2011). "SPO: Structure Preserving Oversampling for Imbalanced Time Series Classification," *ICDM 2011 11th IEEE International Conference on Data Mining*, Vancouver, Canada; pp. 1008-1013.

Das, B. et al. (2015). "RACOG and wRACOG: Two Probabilistic Oversampling Techniques," *IEEE Transactions on Knowledge and Data Engineering*, vol. 27, No. 1; pp. 222-234.

Dangi, A. P. et al. (2015). "Privacy Preservation Measurement through Diversity and Anonymity Using Closeness," *JETIR*, vol. 2, issue 11; pp. 35-40.

Tang, S. et al. (2008). "The Generation Mechanism of Synthetic Minority Class Examples," *2008 International Conference on Information Technology and Applications in Biomedicine*, Shenzhen, China; pp. 444-447.

SYNTHETIC RARE CLASS GENERATION BY PRESERVING MORPHOLOGICAL IDENTITY

PRIORITY CLAIM

This U.S. patent application claims priority under 35 U.S.C. § 119 to: Indian Patent Application No. 201721028875, filed on 14 Aug. 2017. The entire contents of the aforementioned application are incorporated herein by reference.

TECHNICAL FIELD

The embodiments herein generally relate to data classification and more particularly to systems and methods for synthetic rare class generation by preserving morphological identity for facilitating data classification.

BACKGROUND

Data-driven computational method is a challenging task in a scenario wherein rare class examples are scarce. For instance, examples or training datasets of disease class is very less in number compared to examples or training datasets of normal class. Again, fraud credit card events available for a certain type of transaction is very less in number compared to normal transaction events. Existing supervised learning methods perform poorly when one of the class examples is rare in number.

SUMMARY

Embodiments of the present disclosure present technological improvements as solutions to one or more of the above-mentioned technical problems recognized by the inventors in conventional systems.

In an aspect, there is provided a processor implemented method comprising: analyzing a labeled abundant training dataset and labeled rare class training dataset; generating an extended synthetic rare class super dataset based on the analysis using an extended oversampling method; and extracting a subset of the extended synthetic rare class super dataset to obtain a synthetic rare class dataset by maximizing similarity and diversity in the synthetic rare class dataset, wherein maximizing similarity ensures maximizing mutual information and maximizing diversity ensures minimum redundancy in the synthetic rare class dataset such that morphological identity of the synthetic rare class dataset is preserved with respect to the labeled rare class training dataset while maintaining diversity.

In another aspect, there is provided a system comprising: one or more data storage devices operatively coupled to the one or more processors and configured to store instructions configured for execution by the one or more processors to: analyze a labeled abundant training dataset and labeled rare class training dataset; generate an extended synthetic rare class super dataset based on the analysis using an extended oversampling method; and extract a subset of the extended synthetic rare class super dataset to obtain a synthetic rare class dataset by maximizing similarity and diversity in the synthetic rare class dataset, wherein maximizing similarity ensures maximizing mutual information and maximizing diversity ensures minimum redundancy in the synthetic rare class dataset such that morphological identity of the synthetic rare class dataset is preserved with respect to the labeled rare class training dataset while maintaining diversity.

In yet another aspect, there is provided a computer program product comprising a non-transitory computer readable medium having a computer readable program embodied therein, wherein the computer readable program, when executed on a computing device, causes the computing device to: analyze a labeled abundant training dataset and labeled rare class training dataset; generate an extended synthetic rare class super dataset based on the analysis using an extended oversampling method; and extract a subset of the extended synthetic rare class super dataset to obtain a synthetic rare class dataset by maximizing similarity and diversity in the synthetic rare class dataset, wherein maximizing similarity ensures maximizing mutual information and maximizing diversity ensures minimum redundancy in the synthetic rare class dataset such that morphological identity of the synthetic rare class dataset is preserved with respect to the labeled rare class training dataset while maintaining diversity.

In an embodiment of the present disclosure, the one or more hardware processors are further configured to perform extended oversampling method based on a Markov chain model.

In an embodiment of the present disclosure, the labeled abundant training dataset comprises labeled non-anomalous examples and the rare class training dataset comprises labeled anomalous examples.

In an embodiment of the present disclosure, the one or more hardware processors are further configured to perform the step of extracting a subset of the extended synthetic rare class super dataset to obtain a synthetic rare class dataset by: determining a similarity function pertaining to the extended synthetic rare class super dataset to obtain an extended rare class similar dataset; generating a ranked extended rare class similar dataset by ranking elements of the extended rare class similar dataset based on a similarity index associated thereof and sorting in descending order; and determining a diversity function for the ranked extended rare class similar dataset to obtain the synthetic rare class dataset with elements that are top ranked in the ranked extended rare class similar dataset and satisfies the diversity function.

In an embodiment of the present disclosure, the diversity function is based on l-diversity.

In an embodiment of the present disclosure, the synthetic rare class dataset is independent of dimensionality and is signal space rare class dataset.

It is to be understood that both the foregoing general description and the following detailed description are exemplary and explanatory only and are not restrictive of the embodiments of the present disclosure, as claimed.

BRIEF DESCRIPTION OF THE DRAWINGS

The embodiments herein will be better understood from the following detailed description with reference to the drawings, in which.

Figure 1:
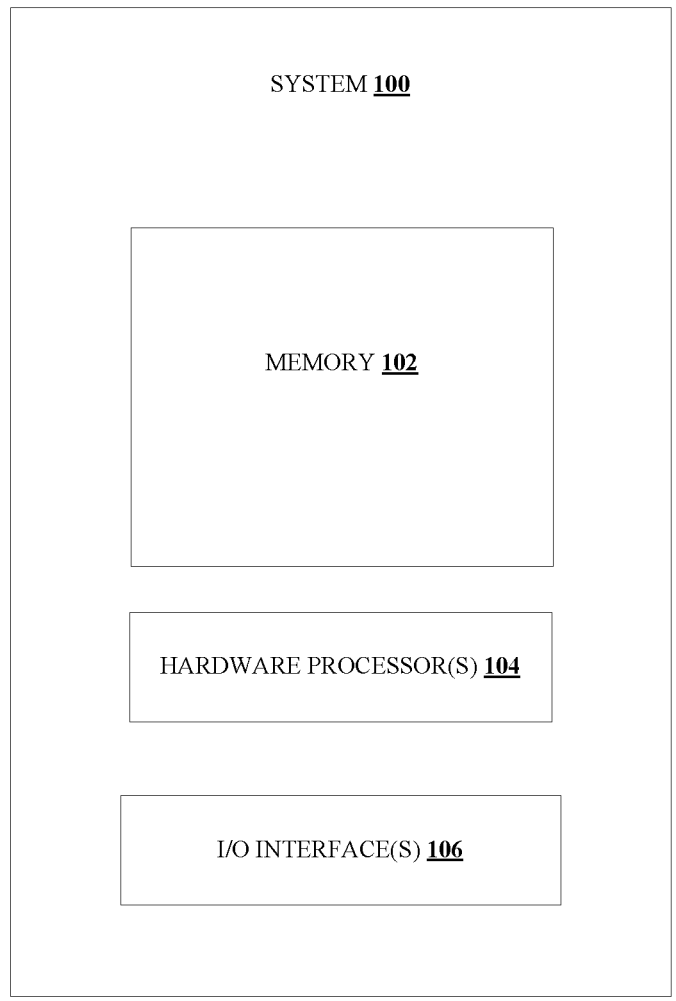
FIG. 1 illustrates an exemplary block diagram of a system for synthetic rare class generation by preserving morphological identity, in accordance with an embodiment of the present disclosure.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

DETAILED DESCRIPTION OF EMBODIMENTS

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those skilled in the art to practice the embodiments herein. Accordingly, the examples should not be construed as limiting the scope of the embodiments herein.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Some embodiments of this disclosure, illustrating all its features, will now be discussed in detail. The disclosed embodiments are merely exemplary of the disclosure, which may be embodied in various forms.

Before setting forth the detailed explanation, it is noted that all of the discussion below, regardless of the particular implementation being described, is exemplary in nature, rather than limiting.

Clinical decision making in data-driven computational methods is a challenging task due to scarcity of negative examples. The main drawback of prior-art is that simple over-sampling of available rare class examples are performed to generate synthetic rare class, which does not ensure diversity in the generated examples. Also, prior-art does not consider preserving morphological identities between the available rare class examples and generated rare class examples, thereby ignoring balancing of performance of the learning method. Systems and methods of the present disclosure ensure diversity (by not merely cloning as in the prior art) in the generated rare class examples while preserving morphological identity to overcome the class imbalance issue of the prior art.

Referring now to the drawings, and more particularly to FIGS. 1 through 4B, where similar reference characters denote corresponding features consistently throughout the figures, there are shown preferred embodiments and these embodiments are described in the context of the following exemplary system and method.

FIG. 1 illustrates an exemplary block diagram of a system 100 for synthetic rare class generation by preserving morphological identity, in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

In an embodiment, the system 100 comprises one or more data storage devices or memory 102 operatively coupled to the one or more processors 104 and is configured to store instructions configured for execution of steps of the method 200 by the one or more processors 104.

Figure 2:
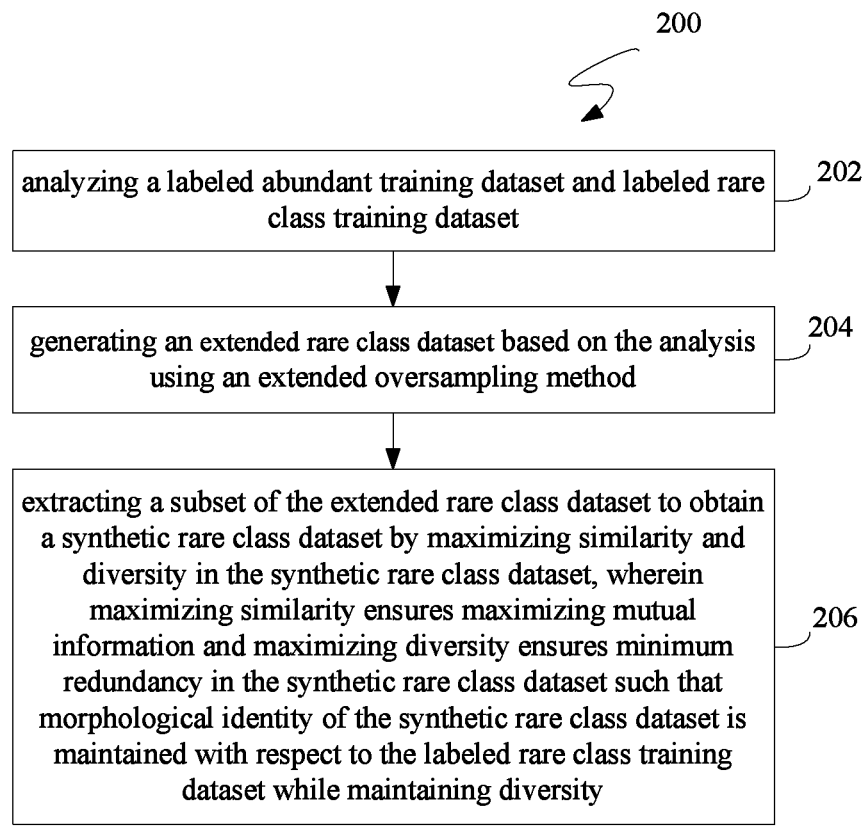
FIG. 2 is an exemplary flow diagram illustrating a computer implemented method for synthetic rare class generation by preserving morphological identity, in accordance with an embodiment of the present disclosure.

FIG. 2 is an exemplary flow diagram illustrating a computer implemented method for synthetic rare class generation by preserving morphological identity, in accordance with an embodiment of the present disclosure. The steps of the method 200 will now be explained in detail with reference to the components of the system 100 of FIG. 1. Table 1 herein below provides notation description used in the present disclosure.

TABLE 1

| Notation | Description |
| --- | --- |
| $X_+$ | labeled abundant training dataset |
| $X_-$ | labeled rare class training dataset |
| $X_{---}$ | extended synthetic rare class super dataset |
| $X_{--}$ | synthetic rare class dataset |

In accordance with an embodiment of the present disclosure, the one or more processors 104 are configured to analyze, at step 202, a labeled abundant training dataset ($\mathbb{X}_+$) and labeled rare class training dataset ($\mathbb{X}_-$). In the context of the present disclosure, the expression "abundant training dataset" refers to a dataset for a class that is available in large numbers. For instance in case of a transaction scenario, positive training dataset in the form of normal transaction events may be available in large numbers. On the contrary, negative training dataset in the form of fraud credit card events may be available in small numbers only and may be referred to as "rare class training dataset". Again in a clinical decision making scenario, disease class examples may be referred to as "rare class training dataset" while normal class examples may be referred to as "abundant training dataset". Accordingly, in an embodiment, the labeled abundant training dataset may refer to labeled non-anomalous examples and the rare class training dataset may refer to labeled anomalous examples. Although this is a generally observed scenario, it may be true otherwise.

In accordance with an embodiment of the present disclosure, the one or more processors 104 are configured to generate, at step 204, an extended synthetic rare class super dataset ($\mathbb{X}_{---}$) based on the analysis using an extended oversampling method. As explained above, a critical problem in anomaly detection is the limited availability of labeled rare class training dataset, which in an embodiment may be labeled anomalous examples. Let $\Pi$, $\pi$ be the cardinality of the labeled abundant training dataset ($\mathbb{X}_+$) and the labeled rare class training dataset ($\mathbb{X}_-$) respectively and $\Pi \gg \pi$.

Let $\mathcal{X} = (\mathbb{X}_+, \mathbb{X}_-)$,
$\mathbb{X}_+ = \{x_i^+\}_{i=1}^{\Pi}$, $\mathbb{X}_- = \{x_i^-\}_{i=1}^{\pi}$, where $x_i^+, x_i^- \in \mathbb{R}^d$, where $\mathbb{R}^d$ represents training instances.

At step 204, a generation function $\mathcal{G}$ generates the extended synthetic rare class super dataset ($\mathbb{X}_{---}$) represented $$\{\mathbb{X}_-\} \xrightarrow{\mathcal{G}} \mathbb{X}_{---} = \{x_i^{---}\}_{i=1}^{\pi++}.$$

One example of generation function $\mathbb{X}$ is that of permutated data generation in Markov chain model, an extended oversampling method. Alternatively, any deterministic model with a known function may be employed. Given the labeled rare class training dataset ($\mathbb{X}_{--}$), some predicted number of states and associated state transition probabilities, the extended synthetic rare class super dataset $X_{---} = \{x_i^{---}\}_{i=1}^{\pi++}$ is generated, where length of [length $(\{x_i^{---}\}_{i=1}^{\pi++})$, $\forall_i$]$\leq$median($\mathbb{X}_-$)$\mp 3$ $\sigma(\mathbb{X}_-)$. Let the cardinality $\Pi$ of the labeled abundant training dataset ($\mathbb{X}_+$) be 500 and the cardinality $\pi$ of the labeled rare class training dataset be $\mathbb{X}_- = \{x_i^-\}_{i=1}^{\pi=20}$. In accordance with the present disclosure, the extended synthetic rare class super dataset ($\mathbb{X}_{---}$) of 10000 instances is firstly generated by the generation function $\mathbb{X}$. From ($\mathbb{X}_{---}$), the synthetic rare class dataset $\mathbb{X}_{--} = \{x_i^{--}\}_{i=1}^{\pi}$ having 500 examples are extracted. Here, in the exemplary embodiment, $\Pi=500$, $\pi=20$ and $\Pi++=10000$.

In physiological signal space, typically a noisy signal consists of four segments: clean segment, motion artifact, random noise and power line interference segment, which correspond to measurement, instrumentation and interference plane respectively. In an embodiment, a Markov model based synthetic signal generation is provided, wherein the Markov model provides a systematic and stochastic method to model the time varying signals. In the Markov model, a future state only depends upon current states, not on predecessor states. This assumption and property makes the Markov model best suited for the generation of noisy/anomalous synthetic data or the rare class training dataset.

Figure 3:
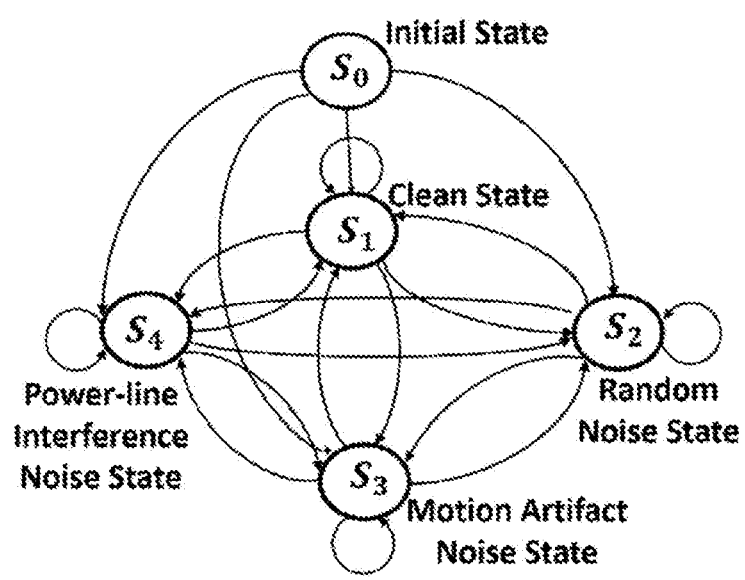
FIG. 3 is an illustration of a Markov chain model for generating an extended synthetic rare class super dataset, in accordance with an embodiment of the present disclosure.

A stochastic process $\{X_n\}$ is called a Markov chain if for all times $n\geq 0$ and all states $i_0, i_1, \ldots j \in S$.

$$P(x_{n+1} = j \mid x_n = i, x_{n-1} = i_{n-1}, \ldots \ldots \ldots, x_0 = i_0) =$$
$$P(x_{n+1=j} \mid x_n = i) = P_{ij}$$

wherein $P_{ij}$ denotes a probability of moving from one state to another state, subject to $\Sigma P_{ij}=1$ and is known as one state Markov chain. FIG. 3 is an illustration of a Markov chain model for generating an extended synthetic rare class super dataset, in accordance with an embodiment of the present disclosure. The illustrated Markov model consists of five states. The state transition matrix is formed from noisy signal instances which are extracted from publicly available sources [Sardouie et al., *IEEE journal of biomedical and health informatics* 2015; Fasshauer and Zhang, *Numerical Algorithms* 2007]. In accordance with the present disclosure, for computation of state transition probabilities, it is assumed that state #2 (S2=random noisy segment) and state #3 (S3=motion artifact) may contribute maximum to noisy signals. Hence, corresponding probabilities are taken higher than other states. Table 2 herein below represents state transition probabilities ($P_{ij}$).

TABLE 2

|       | $S_0$ | $S_1$ | $S_2$ | $S_3$ | $S_4$ |
|-------|-------|-------|-------|-------|-------|
| $S_1$ | 0.05  | 0.05  | 0.05  | 0.05  | 0.1   |
| $S_2$ | 0.4   | 0.5   | 0.3   | 0.4   | 0.3   |
| $S_3$ | 0.5   | 0.4   | 0.6   | 0.5   | 0.5   |
| $S_4$ | 0.05  | 0.05  | 0.05  | 0.05  | 0.1   |

In accordance with an embodiment, generating the extended synthetic rare class super dataset ($\mathbb{X}_{---}$) using the Markov model may be represented as given below.
Input:
 (i) labeled rare class training dataset ($\mathbb{X}_-$)
 (ii) labeled abundant training dataset ($\mathbb{X}_+$)
 (iii) prior knowledge as represented in Table 2 above and FIG. 3
  (a) Different transition states $S=\{S_i\}_{i=1}^n$
  (b) State transition probabilities $P_{ij}$; $\Sigma P_{ij}=1$
Output: extended synthetic rare class super dataset ($\mathbb{X}_{---}$)
Method:
1. Let length of the abundant training dataset ($\mathbb{X}_+$) be $L_p = \{1_1^p, 1_2^p, \ldots 1_\Pi^p\}$.
2. Construct the Markov chain model (Refer FIG. 3)
3.
  $S_0$, $S_1$: Randomly selected from $\mathbb{X}_+$
  $S_2$: Additive white noisy signal from Gaussian distribution
  $S_3$: Typical motion artifact samples [Fraser et al., *IEEE transactions on Instrumentation and Measurement* 2014; Fasshauer and Zhang, *Numerical Algorithms* 2007].
  $S_4$: Powerline Interference (60 Hz).
4. Construct $L_r = \{1_1^r, 1_2^r, \ldots 1_\pi^r\}$, where $1_i^r$, i=1, 2, . . . , $\Pi$ be the length the generated extended synthetic rare class super dataset such that $\Sigma L_p = \Sigma L_r$.

5. $\mathbb{X}_i^{---} = \{S_0, S_k\}_i$, order in which $S_k$; $k \in [1, 4]$ selected, based on State Transition probabilities {Refer Table 2}; E.g. $x_i^{---} = \{S_0, S_2, S_3, S_1, S_4\}_i$ where length $(x_i^{---}) = l_i^r$.

It may be noted that the method described herein above, imposes restriction on the signal length (step 4) and arbitrary length is not permitted as in the case of the art.

In accordance with an embodiment of the present disclosure, the one or more processors 104 are configured to extract, at step 206, a subset of the extended synthetic rare class super dataset ($\mathbb{X}_{---}$) to obtain the synthetic rare class dataset ($\mathbb{X}_{--}$) by maximizing similarity $\mathcal{S}$ and diversity $\mathcal{D}$ in the synthetic rare class dataset, wherein maximizing similarity ensures maximizing mutual information (explained hereinafter) and maximizing diversity ensures minimum redundancy in the synthetic rare class dataset such that morphological identity of the synthetic rare class dataset is preserved with respect to the labeled rare class training dataset while maintaining diversity. In the context of the present disclosure, morphological identity refers to characteristics associated with the available rare class dataset that are preserved in the synthetic rare class dataset while preserving diversity.

Dissimilarity property $\mathcal{B}$ with $\mathbb{X}_+$ may be represented as given below.

$$\text{maximize}_{x_i^+, x_i^- \in \mathbb{R}^d} (\mathcal{S}(\mathbb{X}_-), \mathcal{D}(\mathbb{X}_-), \mathcal{B}(\mathbb{X}_+)) \quad (1)$$

with the assumption that the generated synthetic rare class dataset ($\mathbb{X}_{--}$) would be similar yet not redundant with the labeled rare class training dataset ($\mathbb{X}_-$) but distinct from the labeled abundant training dataset ($\mathbb{X}_+$). In accordance with the present disclosure, it is further assumed that the labeled abundant training dataset ($\mathbb{X}_+$) and the labeled rare class training dataset ($\mathbb{X}_-$) are independent and subsequently, similarity $\mathcal{S}$ among $\mathbb{X}_-$ and dissimilarity $\mathcal{B}$ between ($\mathbb{X}_+$) and ($\mathbb{X}_-$) are equivalent. For simplicity of explanation, it is assumed that satisfying similarity is practically sufficient to satisfying dissimilarity and accordingly, the condition may be omitted from further consideration. The problem addressed in the present disclosure is therefore to generate the synthetic rare class dataset $\mathbb{X}_{--} = \{x_i^{--}\}_{i=1}^{\pi}$ from the labeled rare class training dataset $\mathbb{X}_- = \{x_i^-\}_{i=1}^{\pi}$, where $\Pi \gg \pi$. Let, the extended synthetic rare class super dataset $\mathbb{X}_{---} = \{x_i^{---}\}_{i=1}^{\pi++}$, $\Pi++ \gg \Pi$ be the universe of the synthetic rare class dataset ($\mathbb{X}_{--}$) generated. The problem is to find ($\mathbb{X}_{--}$) from the universe ($\mathbb{X}_{---}$) such that equation (1) is satisfied.

In an embodiment, the step of extracting a subset of the extended synthetic rare class super dataset ($\mathbb{X}_{---}$) to obtain a synthetic rare class dataset ($\mathbb{X}_{--}$) comprises firstly determining a similarity function pertaining to the extended synthetic rare class super dataset ($\mathbb{X}_{---}$) to obtain an extended rare class similar dataset and then generating a ranked extended rare class similar dataset by ranking elements of the extended rare class similar dataset based on a similarity index associated thereof and sorting in descending order. In accordance with the present disclosure, one example of the similarity function may be constructed as: Find mutual information $$\mathbb{I}(x; y) = \Sigma_{x \in \mathbb{X}_{---}} \Sigma_{y \in \mathbb{X}_-} p(x, y) \log_2 \frac{p(x, y)}{p(x)p(y)}$$

for each of $\mathbb{X}_{---}$ with each of $\mathbb{X}_-$ that spawns $\Pi++ \times \pi$ in $\mathbb{I}(\mathbb{X}_{---}; \mathbb{X}_-)$. There are $\pi$ number of $\mathbb{I}(x_i^{---}; \mathbb{X}_-)$ for each i. Then, find the cluster centroid $\mathcal{C}_i^{---}$ that contains higher number of cluster elements when performing k-means (k=2) clustering on $\mathbb{I}(x_i^{---}; \mathbb{X}_-)$. For example, let there be 20 number of labeled rare class training dataset ($\mathbb{X}_-$), $\pi=20$: $\mathbb{X}_- = \{x_i^-\}_{i=1}^{\pi=20}$. The generation function $\mathbb{X}$ generates 10000 extended synthetic rare class super dataset, where: $\mathbb{X}_{---} = \{x_i^{---}\}_{i=1}^{\pi=10000}$, $\Pi++ \times \pi = 200000$. For each computed $\mathbb{I}(x_i^{---}; \mathbb{X}_-)$, $\forall i = \{1, 2, \ldots, \pi=20\}$ total 20 mutual information values for each of the generated: $\mathbb{X}_{---} = \{x_i^{---}\}_{i=1}^{\pi=10000}$ are 2-means clusterd. The cluster centroid $\mathcal{C}_i^{---}$ that contains higher number of cluster elements of each $\mathbb{I}(x_i^{---}; \mathbb{X}_-)$ set is marked as the similarity index of $\mathbb{X}_i^{---}$ on $\mathbb{X}_-$. $\mathbb{X}_i^{---}$s are ranked in descending order sorting of the similarity indices. Let, the sorted order of $\mathbb{X}_{---}$ be $\mathbb{X}_{---}^{similar}$.

After the ranked extended rare class similar dataset is generated, a diversity function is determined for the ranked extended rare class similar dataset to obtain the synthetic rare class dataset with elements that are top ranked in the ranked extended rare class similar dataset and satisfies the diversity function. Accordingly, the diversity function is determined on $\mathbb{X}_{---}^{similar}$ and $\mathbb{X}_{---}^{similar+diversed}$ is identified that are both ranked high in $\mathbb{X}_{---}^{similar}$ and significantly diverse. Thus, $\mathbb{X}_{---}^{similar+diversed} \subseteq \mathbb{X}_{---}^{similar}$ and $\mathbb{X}_{---}^{similar+diversed} = \mathbb{X}_{--} = \{x_i^{--}\}_{i=1}^{\pi}$, the generated synthetic rare class dataset. One example of the diversity function may be constructed as: Find $X_{--} = \{x_i^{--}\}_{i=1}^{\pi}$ set from $\mathbb{X}_{---}^{similar}$ which are l-diverse (Machanavajjhala; 2007) and $X_{--}$ contains the top-ranked in $\mathbb{X}_{---}^{similar}$ in each of the l-diverse groups. Definition l-diversity: A group is l-diverse if each of the l different group $\mathcal{L}$'s entropy $\geq \log_2$ l:

$$\Sigma_{s \in S} \mathcal{P}(\mathcal{L}, s) \log_2 \frac{1}{\mathcal{P}(\mathcal{L}, s)} \geq \log_2 l.$$

After constructing l-diverse groups from $\mathbb{X}_{---}^{similar}$, where $l = \Pi^{1/4}$, $\mathbb{X}_{---}^{similar+diversed} \{x_i^{--}\}_{i=1}^{\pi}$ is formed taking the top ranked corresponds $\mathbb{X}_{---}^{similar}$ from each of the l groups such that total number of elements chosen is $\Pi$.

Figure 4A:
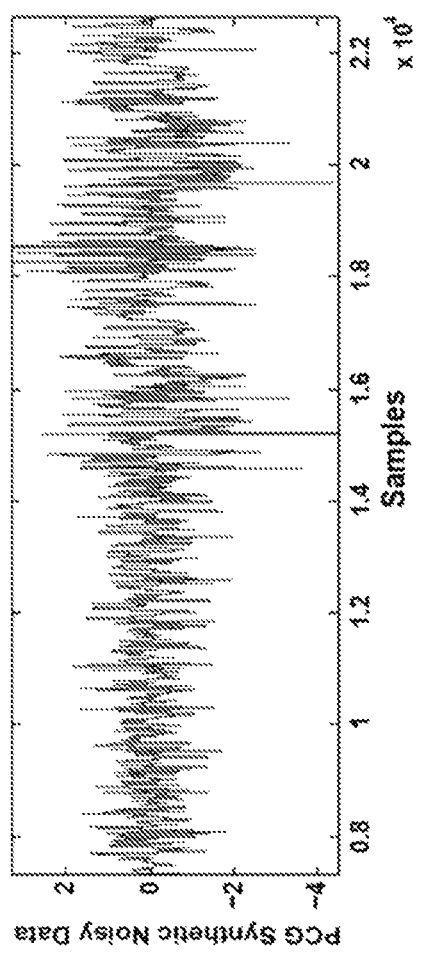
FIG. 4A and FIG. 4B illustrate synthetically generated rare class dataset in accordance with an embodiment of the present disclosure and physiological real-life labeled rare class data respectively.
Figure 4B:
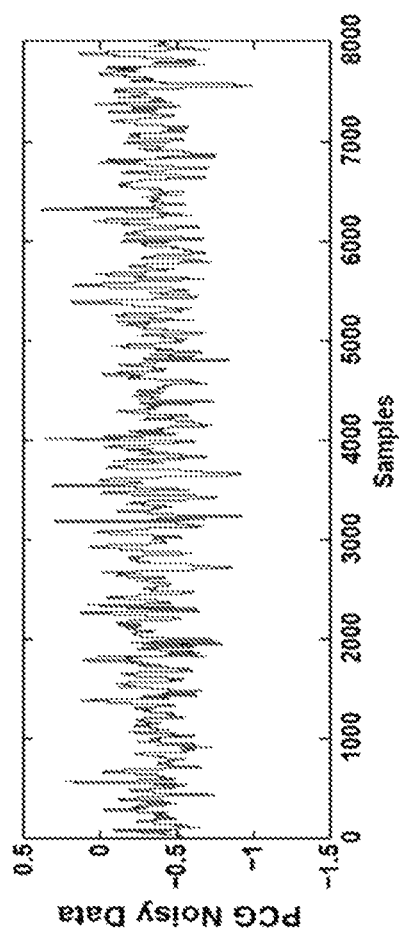

FIG. 4A and FIG. 4B illustrate synthetically generated rare class dataset in accordance with an embodiment of the present disclosure and physiological real-life labeled rare class data respectively. As illustrated, the method of the present disclosure facilitates close capture of real-life noisy physiological signals, which confirms the assumption $\mathcal{X}_{real-life\ noise} \sim \mathcal{F}_x^{synthetic-noise}$. It is observed that morphological identities are closely preserved in the generated synthetic rare class dataset (FIG. 4A) when compared with the real-life noisy physiological signals (FIG. 4B).

Thus in accordance with the present disclosure, systems and methods of the present disclosure facilitate addressing the class imbalance problem in applications such as identifying noisy phonocardiogram (PCG) signals. The present disclosure deals with signal (time-series) space rare-class dataset as compared to prior art that deal with feature space rare-class dataset. The subset of the extended synthetic rare class super dataset is extracted without reducing the dimensionality (feature space) of the dataset, thereby making the step of obtaining the synthetic rare class dataset independent of the dimensionality properties of the datasets and non-parametric.

The written description describes the subject matter herein to enable any person skilled in the art to make and use the embodiments of the present disclosure. The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments of the present disclosure may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules comprising the system of the present disclosure and described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device. The various modules described herein may be implemented as software and/or hardware modules and may be stored in any type of non-transitory computer readable medium or other storage device. Some non-limiting examples of non-transitory computer-readable media include CDs, DVDs, BLU-RAY, flash memory, and hard disk drives.

Further, although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A processor implemented method (200) comprising:
analyzing a labeled abundant training dataset ($\mathbb{X}_+$ that refers to a training dataset for a class available in more numbers and labeled rare class training dataset ($\mathbb{X}_-$) that refers to a training dataset with limited availability compared to the training dataset (202);
generating an extended synthetic rare class dataset ($\mathbb{X}_{---}$) based on the analysis using an oversampling method (204) based on Markov chain model providing a systematic and a stochastic method to model time varying signals, wherein in the Markov chain model, a future state only depends on current state, not on predecessor states; and
extracting a subset of the extended synthetic rare class dataset ($\mathbb{X}_{---}$) to obtain a synthetic rare class dataset ($\mathbb{X}_{--}$) with respect to similarity and diversity in the synthetic rare class dataset ($\mathbb{X}_{--}$) and preserving morphological identity of the synthetic rare class dataset ($\mathbb{X}_{--}$) with respect to the labeled rare class training dataset ($\mathbb{X}_-$) while maintaining diversity (206) and facilitates addressing class imbalance problem in applications such as identifying real-life noisy physiological time-series signals,
wherein the subset of the extended synthetic rare class dataset is extracted without reducing dimensionality of the dataset, thereby making the step of obtaining the synthetic rare class dataset independent of dimensionality properties and is signal space rare class dataset, wherein the real-life noisy physiological time-series signals are phonocardiogram (PCG) signals.

2. The processor implemented method of claim 1, wherein the step of extracting a subset of the extended synthetic rare class dataset to obtain a synthetic rare class dataset comprises:
determining a similarity function pertaining to the extended rare class dataset to obtain an extended rare class similar dataset;
generating a ranked extended rare class similar dataset by ranking elements of the extended rare class similar dataset based on a similarity index associated thereof and sorting in descending order; and
determining a diversity function for the ranked extended rare class similar dataset to obtain the synthetic rare class dataset with elements that are top ranked in the ranked extended rare class similar dataset and satisfies the diversity function.

3. The processor implemented method of claim 2, wherein the diversity function is based on l-diversity.

4. A system (100) comprising:
one or more data storage devices (102) operatively coupled to one or more hardware processors (104) and configured to store instructions configured for execution by the one or more hardware processors to:
analyze a labeled abundant training dataset ($\mathbb{X}_+$) that refers to a training dataset for a class available in more numbers and labeled rare class training dataset ($\mathbb{X}_-$) that refers to a training dataset with limited availability compared to the training dataset;
generate an extended synthetic rare class dataset ($\mathbb{X}_{---}$) based on the using an extended oversampling method based on Markov chain model providing a systematic and a stochastic method to model time varying signals, wherein in the Markov chain model, a future state only depends on current state, not on predecessor states; and
extract a subset of the extended synthetic rare class dataset ($\mathbb{X}_{---}$) to obtain a synthetic rare class dataset ($\mathbb{X}\_\_$), with respect to similarity and diversity in the synthetic rare class dataset ($\mathbb{X}\_\_$) and preserving morphological identity of the synthetic rare class dataset ($\mathbb{X}\_\_$) with respect to the labeled rare class training dataset ($\mathbb{X}\_$) while maintaining diversity and facilitates addressing class imbalance problem in applications such as identifying real-life noisy physiological time-series signals, wherein the subset of the extended synthetic rare class dataset is extracted without reducing dimensionality of the dataset, thereby making the step of obtaining the synthetic rare class dataset independent of dimensionality properties and is signal space rare class dataset, wherein the real-life noisy physiological time-series signals are phonocardiogram (PCG) signals.

5. The system of claim 4, wherein the one or more hardware processors are further configured to perform extended oversampling method based on Markov chain model.

6. The system of claim 4, wherein the one or more hardware processors are further configured to perform the step of extracting a subset of the extended synthetic rare class dataset to obtain a synthetic rare class dataset by:
   determining a similarity function pertaining to the extended rare class dataset to obtain an extended rare class similar dataset;
   generating a ranked extended rare class similar dataset by ranking elements of the extended rare class similar dataset based on a similarity index associated thereof and sorting in descending order; and
   determining a diversity function for the ranked extended rare class similar dataset to obtain the synthetic rare class dataset with elements that are top ranked in the ranked extended rare class similar dataset and satisfies the diversity function.

7. The system of claim 6, wherein the diversity function is based on l-diversity.

8. A computer program product comprising a non-transitory computer readable medium having a computer readable program embodied therein, wherein the computer readable program, when executed on a computing device, causes the computing device to:
   analyze a labeled abundant training dataset ($\mathbb{X}_+$) that refers to a training dataset for a class available in more numbers and labeled rare class training dataset ($\mathbb{X}\_$) that refers to a training dataset with limited availability compared to the training dataset;
   generate an extended synthetic rare class dataset ($\mathbb{X}\_\_\_$) based on the analysis using an oversampling method based on Markov chain model providing a systematic and a stochastic method to model time varying signals, wherein in the Markov chain model, a future state only depends on current state, not on predecessor states; and
   extract a subset of the extended synthetic rare class dataset ($\mathbb{X}\_\_\_$) to obtain a synthetic rare class dataset ($\mathbb{X}\_\_$), with respect to similarity and diversity in the synthetic rare class dataset ($\mathbb{X}\_\_$) and preserving morphological identity of the synthetic rare class dataset ($\mathbb{X}\_\_$) with respect to the labeled rare class training dataset ($\mathbb{X}\_$) while maintaining diversity and facilitates addressing class imbalance problem in applications such as identifying real-life noisy physiological time-series signals,
   wherein the subset of the extended synthetic rare class dataset is extracted without reducing dimensionality of the dataset, thereby making the step of obtaining the synthetic rare class dataset independent of dimensionality properties and is signal space rare class dataset, wherein the real-life noisy physiological time-series signals are phonocardiogram (PCG) signals.

* * * * *